(12) United States Patent
Cabanis et al.

(10) Patent No.: US 8,866,471 B2
(45) Date of Patent: Oct. 21, 2014

(54) PROBE FOR INSPECTING THE SURFACE OF A CIRCUMFERENTIAL SLOT IN A TURBOJET DISK BY MEANS OF EDDY CURRENTS

(75) Inventors: Patrick Cabanis, Ozouer le Voulgis (FR); Sandra Cheynet, Le Plessis Pate (FR); Patrick Gaisnon, Cannes Ecluse (FR); Luc Ravize, Bordes (FR)

(73) Assignee: SNECMA, Paris (FR)

( * ) Notice: Subject to any disclaimer, the term of this patent is extended or adjusted under 35 U.S.C. 154(b) by 674 days.

(21) Appl. No.: 12/992,514

(22) PCT Filed: May 13, 2009

(86) PCT No.: PCT/FR2009/050877
§ 371 (c)(1),
(2), (4) Date: Nov. 12, 2010

(87) PCT Pub. No.: WO2009/147351
PCT Pub. Date: Dec. 10, 2009

(65) Prior Publication Data
US 2011/0062954 A1    Mar. 17, 2011

(30) Foreign Application Priority Data
May 14, 2008   (FR) ...................... 08 53109

(51) Int. Cl.
*G01N 27/82* (2006.01)
*G01N 27/90* (2006.01)

(52) U.S. Cl.
CPC .......... *G01N 27/904* (2013.01); *G01N 27/9033* (2013.01)
USPC ....................................... 324/238

(58) Field of Classification Search
USPC ........................................... 324/242
See application file for complete search history.

(56) References Cited

U.S. PATENT DOCUMENTS

| 5,315,234 | A | * | 5/1994 | Sutton et al. | ................... 324/242 |
| 5,442,286 | A | | 8/1995 | Sutton, Jr. et al. | |
| 5,781,007 | A | | 7/1998 | Partika et al. | |
| 6,152,698 | A | * | 11/2000 | Gregg et al. | ................... 416/215 |
| 7,466,126 | B2 | * | 12/2008 | Kliman et al. | ................ 324/219 |

(Continued)

FOREIGN PATENT DOCUMENTS

| DE | 25 30 816 | 1/1977 |
| EP | 0 577 244 | 1/1994 |
| EP | 1 245 953 | 10/2002 |

OTHER PUBLICATIONS

U.S. Appl. No. 12/211,357, filed Sep. 16, 2008, Briffa, et al.

(Continued)

*Primary Examiner* — Arleen M Vazquez
*Assistant Examiner* — Feba Pothen
(74) *Attorney, Agent, or Firm* — Oblon, Spivak, McClelland, Maier & Neustadt, L.L.P.

(57) ABSTRACT

A probe for eddy current monitoring of the surface of a circumferential slot formed in a turbojet disk. The probe includes a stem fastened to a support and a first multi-element sensor constrained to move with the stem and configured to be inserted into the circumferential slot to perform the inspection, and a second multi-element sensor. The two multi-element sensors are disposed back to back, and the stem of the probe is mounted to pivot about its own axis to enable the two multi-element sensors to be inserted in the slot.

9 Claims, 2 Drawing Sheets

(56) References Cited

U.S. PATENT DOCUMENTS

| | | | |
|---|---|---|---|
| 7,659,715 B2 * | 2/2010 | Briffa et al. | 324/240 |
| 7,768,259 B2 | 8/2010 | Cabanis et al. | |
| 7,800,364 B2 | 9/2010 | Briffa et al. | |
| 2002/0135363 A1 | 9/2002 | Trantow et al. | |

OTHER PUBLICATIONS

International Search Report issued Jan. 22, 2010 in PCT/FR09/50877 filed May 13, 2009.

Japanese Office Action issued Oct. 15, 2013 in Patent Application No. 2011-508983.

* cited by examiner

PROBE FOR INSPECTING THE SURFACE OF A CIRCUMFERENTIAL SLOT IN A TURBOJET DISK BY MEANS OF EDDY CURRENTS

BACKGROUND OF THE INVENTION

1. Field of the Invention

The present invention relates to a probe for inspecting surface anomalies and irregularities of a circumferential slot in a turbojet disk by means of eddy currents.

2. Description of the Related Art

The circumferential slot of a turbojet disk is intended to receive a series of blades and it is subjected to high levels of stress when the turbojet is in operation, in particular on its faces of concave angular shape (referred to below as the "side faces" of the slot). As a result, slots of this type require very regular inspection. Given the poor accessibility of the side faces, it is common practice to verify their surface state by performing inspection by means of eddy currents. This type of inspection consists in scanning the surface for examination by means of a probe fitted with a sensor that, by creating an electromagnetic field, produces eddy currents in the part under inspection. In practice, it is usually the part that is caused to pivot while the probe remains stationary on its support. When the surface of the slot presents anomalies, the eddy current flux is altered and the sensor generates an electrical signal that corresponds to the alteration. The amplitude of the signal is proportional to the magnitude of the detected surface anomaly. In order to ensure that this proportionality remains true, it is nevertheless necessary for contact between the surface for inspection and the eddy current probe to be maintained continuously.

Shoe probes are already known that are made up of a single-element sensor fastened to the end of a stem that is capable of being moved by means of its support along the axial and radial directions of the turbojet disk. That type of probe requires the probe to be moved stepwise along the profile under inspection, each movement of the probe in the axial direction of the disk being followed by a turning movement of the disk or of the probe so as to scan the entire surface of the slot. The single-element sensor is inserted into the slot, put into contact with the surface for inspection, and then the part is caused to perform one complete revolution so that a complete circumferential strip of the slot is examined. That operation is then repeated several times, changing the position of the single-element sensor on the surface for inspection each time so as to scan the entire surface of the slot. Since the single-element sensor is asymmetrical, after one side face of the slot has been inspected, it is necessary to turn the sensor about in order to examine the opposite side. The result enabling the surface state of the slot to be evaluated is obtained by incrementing the results of the various measurement performed using the single-element sensor.

In order to reduce the number of measurements that are needed for a full inspection of the surface of a slot, proposals have been made to replace the single-element sensor of the probe with a multi-element sensor of shape that advantageously matches the profile of one of the side faces of the slot. The entire slot can then be inspected in only two operations (one complete revolution for each side face of the slot, with the sensor being turned around between the two operations).

Those two systems present several drawbacks. The large number of measurements and calculations, and also the difficulty in positioning the sensor against the surface for examination, decrease the accuracy of the results. Furthermore, insofar as the known system allows only one side of the slot to be inspected, problems associated with the stem flexing appear over time, thereby falsifying the measurement results because of the multi-element sensor being poorly oriented relative to the surface for inspection.

BRIEF SUMMARY OF THE INVENTION

The present invention relates in particular to an improvement of a probe having a multi-element sensor.

The invention proposes limiting the number of operations needed for eddy current inspection of the surfaces of circumferential slots in turbojet disks. Another object of the invention is to enable the probe to be well positioned inside the slot. The invention thus serves to reduce considerably the duration of the inspection and to increase the accuracy of the results.

Firstly, the invention provides a probe for eddy current monitoring of the surface of a circumferential slot formed in a turbojet disk, the probe comprising a stem fastened to a support and a first multi-element sensor constrained to move with the stem and intended to be inserted into said circumferential slot in order to perform the inspection, the probe being characterized in that it further comprises a second multi-element sensor, in that the two multi-element sensors are disposed back to back, and in that said stem is mounted to pivot about its own axis to enable the two multi-element sensors to be inserted in said slot.

Each multi-element sensor is for coming into contact with a respective one of the side faces of the slot. These multi-element sensors comprise a plurality of elements delivering high frequency signals corresponding to the level of damage to the surface being inspected. These signals are acquired in real time, with a digital eddy current generator being used to send them, to receive them, and to demodulate them. These signals are then transformed into images by software processing so that they can be interpreted by the operator.

The set of two multi-element sensors placed back to back presents a width that is necessarily greater than the width of the inlet to the slot. To enable the probe to be inserted in the slot, the stem is mounted pivotally on its support, e.g. by a ball slideway and spring system.

Advantageously, the two multi-element sensors are urged resiliently in opposite directions, so as to provide good contact between the multi-element sensors and the opposite surfaces for inspection.

Preferably, at least one spring is interposed between the two multi-element sensors.

According to a preferred provision of the invention, each multi-element sensor is of a shape that corresponds to the profile of a face of the slot for inspection.

According to another preferred provision of the invention, the two multi-element sensors are held back to back and are connected to the stem by a sliding arrangement.

Secondly, the invention provides a method for eddy current inspection of the surface of a circumferential slot formed in a turbojet disk by means of a probe as described above, the method being characterized in that it comprises the steps consisting in:

a) positioning the two sensors in register with the opening of the slot so that a common axis of the sensors extends perpendicularly to the axis of the disk;

b) moving the probe in a radial direction of the disk towards the inside of the slot so as to insert the two multi-element sensors in said slot; then c) causing the stem to pivot through an angle of 90° so that the multi-element sensors come into contact with the side faces of the slot for inspection; and finally d) scanning the entire surface of the circumferential slot.

Advantageously, during step d), the probe remains stationary and the disk is turned through an angle of 360°.

By means of the provisions of the present invention, it is possible to acquire all of the data in a single scanning revolution of the probe. The two side faces of the slot are inspected simultaneously by the two multi-element sensors. Furthermore, good contact may be maintained between the multi-element sensors and the disk by means of one or more return springs arranged between the two sensors that are placed back to back. By reducing the number of inspection operations, the probe of the invention reduces the influence of the human factor on the measurement results, thereby limiting risks of error. By providing good contact between the probe and the side faces of the slot, the invention also enables the measurement results to be refined. Finally, in spite of the poor access to the shape that is to be inspected, and because of the automatic self-balancing between the sensors placed back to back, it is possible to avoid phenomena of the stem flexing, which can lead to contact being lost between the sensors and the surfaces for inspection.

BRIEF DESCRIPTION OF THE SEVERAL VIEWS OF THE DRAWINGS

The invention can be well understood and its advantages appear better on reading the following detailed description of an embodiment given by way of non-limiting example. The description refers to the accompanying drawings, in which.

DETAILED DESCRIPTION OF THE INVENTION

Figure 1:
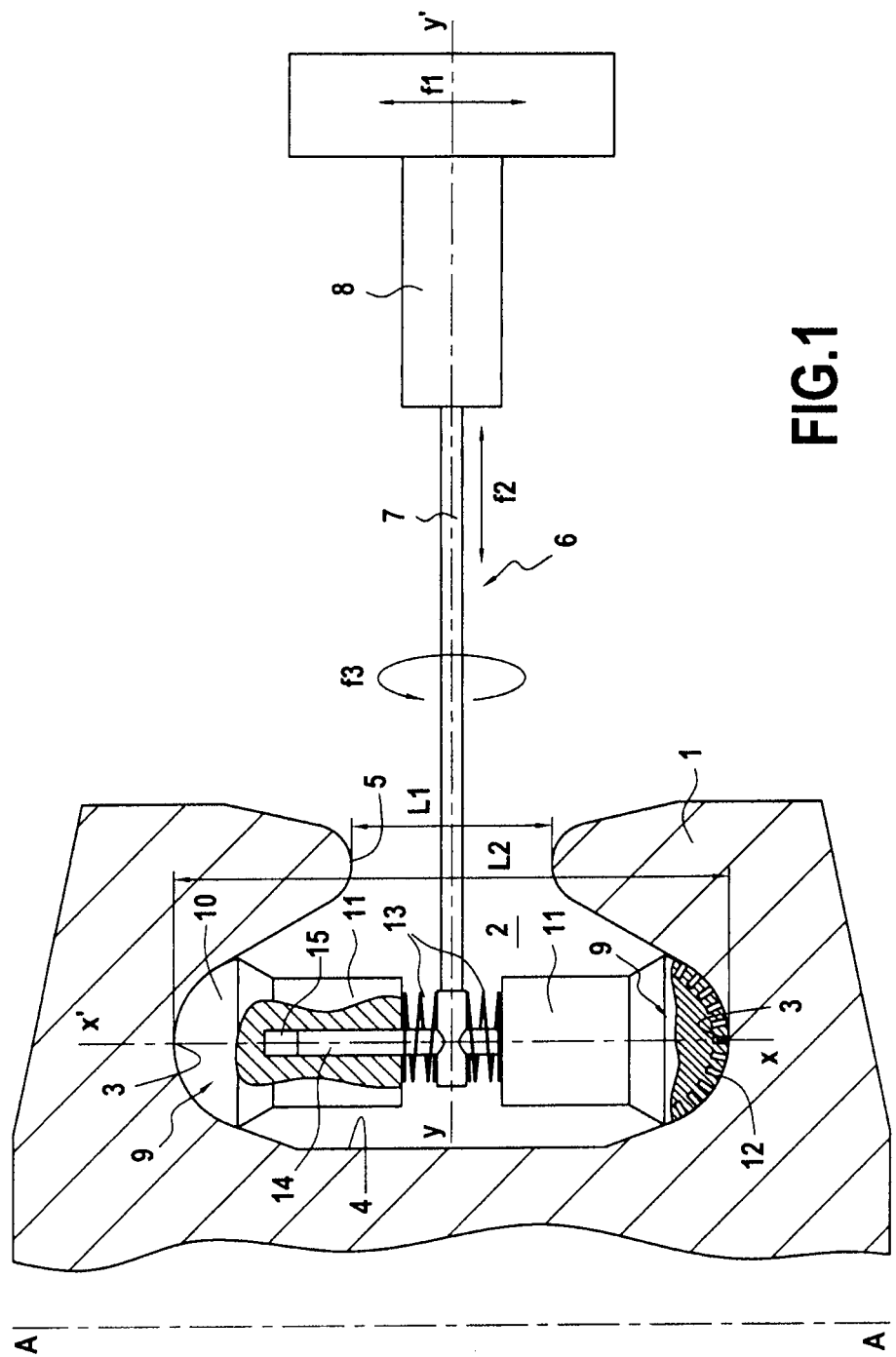
FIG. 1 is a fragmentary section view of a circumferential slot in a turbojet disk, with a probe of the invention shown inserted therein.

FIG. 1 shows a portion of a turbojet disk 1 having a circumferential slot 2 machined therein for receiving a series of blades. The slot has a substantially cylindrical central face 4 about an axis A-A, and two side faces 3 of concave annular shape. The slot 2 opens out via an annular opening 5 of width $L_1$ measured in the axial direction. The width $L_1$ of the opening 5 is less than the greatest width $L_2$ of the slot 2 measured in the axial direction, i.e. between its side faces 3.

A probe of the present invention is described with reference to FIG. 1. The probe 6 is constituted by a stem 7, a support 8, and two multi-element sensors 9. Arrows f1, f2, and f3 represent the degrees of freedom of the stem 7, determined by ball slideways and springs that are not shown. These degrees of freedom are defined below with reference of the frame of reference of the turbojet disk. In particular, arrow f1 corresponds to the stem being moved along the axis of the disk, arrow f2 corresponds to the stem being moved radially, while f3 designates the stem pivoting about its own axis y-y' that extends in the radial direction of the disk 1. At the opposite end of the stem 7, there are fastened two multi-element sensors 9 that are placed back to back, symmetrically about the axis y-y' of the stem. The symmetry of the two sensors contributes to the probe 6 being self-balancing, thus making it possible to avoid phenomena of the stem flexing and thus to maintain good contact between the sensors 9 and the faces 3 of the slot for inspection. Each sensor 9 is constituted by a contact portion 10 and by an attachment portion 11. The contact portion 10 presents a profile that corresponds substantially to the profile of the side face 3 that is to be scanned. As shown in FIG. 1, the contact portion 10 presents a plurality of elements 12 delivering high frequency signals corresponding to the level of damage to the surface with which they come into contact. The attachment portion 11 is intended to receive the means for mounting the sensor 9 relative to the stem 7. In FIG. 1, the sensors 9 are connected to the stem 7 via two return springs 13. A sliding guide 14 is also provided to maintain the two sensors 9 back to back in a plane perpendicular to the axis y-y' of the stem 7. This guide 14 is constituted by two rods sliding in bores 15 formed in the attachment portions 11 of corresponding ones of the sensors 9, the bores 15 of the two sensors 9 being placed in line with each other.

The eddy current inspection method implemented by means of the probe described above is described below with reference to FIGS. 2A to 2C.

Figure 2A:
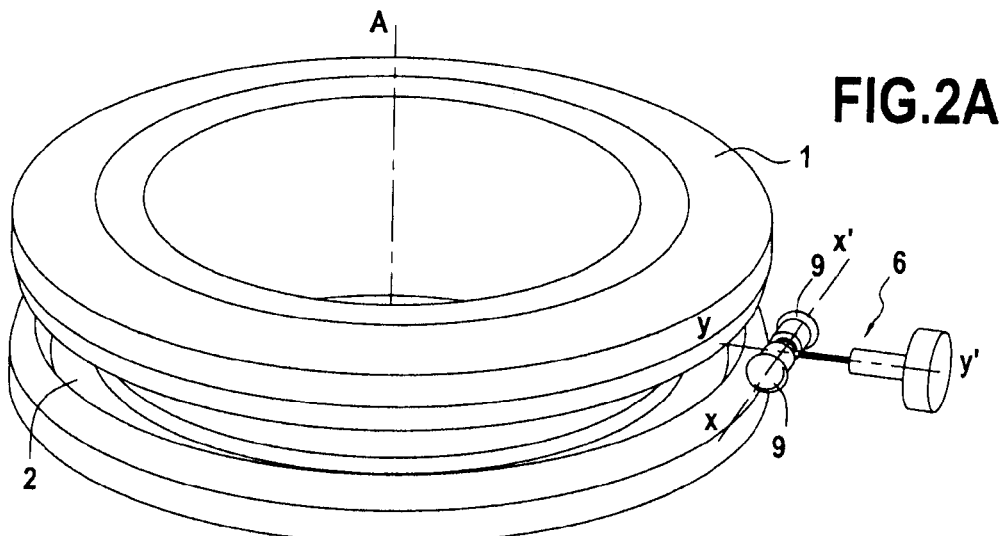
FIGS. 2A to 2C show the successive steps of the method of the invention for inspecting the surface of a circumferential slot.

FIG. 2A shows the turbojet disk 1 in which there is formed the slot 2 having a surface state that is to be inspected. The probe 6 is moved in the direction $f_1$ until its axis lies in the midplane of the circumferential slot 2. The probe is then pivoted in the direction of arrow $f_3$ so that the two sensors 9 that are disposed back to back are both placed facing the opening of the slot 2, their common axis x-x' being perpendicular to the axis A-A of the disk.

Figure 2B:
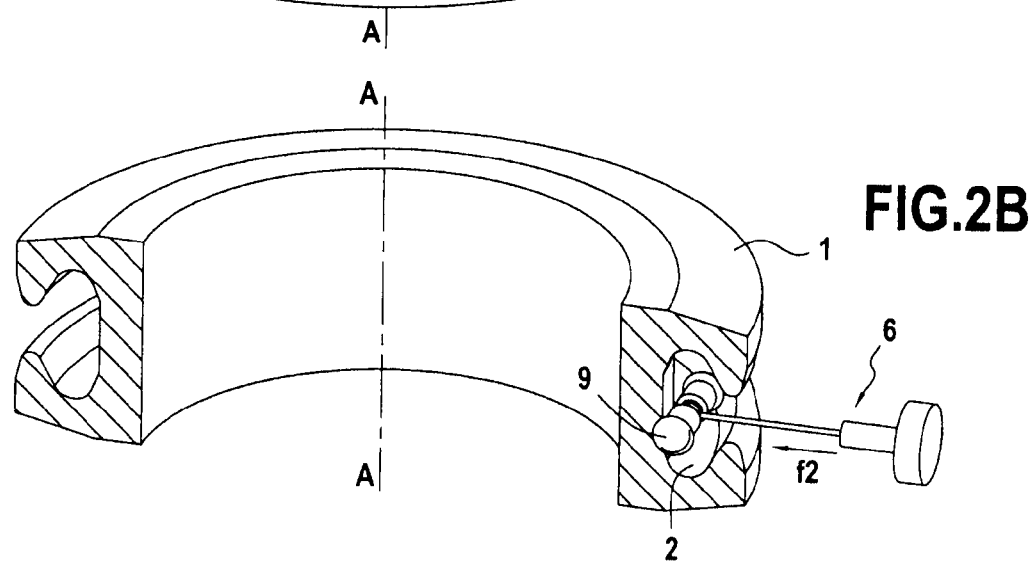

As shown in FIG. 2B, the two sensors 9 of the probe 6 are then inserted into the slot 2 by moving the stem 7 in the radial direction $f_2$.

Figure 2C:
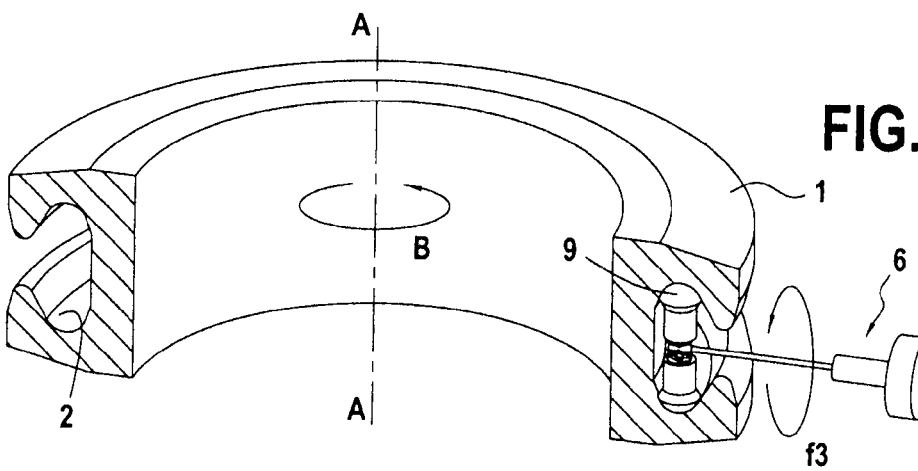

FIG. 2C shows the positioning of the sensors 9 against the side faces 3 of the slot 2. For this purpose, the stem 7 is pivoted through an angle of 90° about its own axis y-y', such that the common axis x-x' of the two sensors becomes parallel to the axis A-A of the turbojet disk 1. During pivoting of the stem 7, the sensors 9 come into abutment against the side faces 3 of the slot 2 prior to being properly positioned on the axis A-A of the disk 1. From this instant, and until the sensors 9 are finally positioned, the return spring 13 becomes compressed, forcing the sensors 9 into contact against the side faces 3 of the slot 2. The return springs contribute to maintaining good contact between the sensors 9 and the surface 3 of the slot 2, and consequently to obtaining an electrical signal that is accurately proportional to the level of damage to the surface.

Arrow B in FIG. 2C illustrates the operation of scanning the slot 2. Preferably, the probe 6 remains stationary while the turbojet disk 1 turns about its own axis A-A.

During circumferential scanning of the slot 2, both sensors 9 deliver respective high frequency signals proportional to the levels of damage of the side faces 3 of the slot 2. These signals are subsequently filtered and displayed on a screen in the form of images representative of the results obtained and suitable for use by an operator.

The invention claimed is:

1. An eddy current probe for monitoring a surface of a circumferential slot formed in a turbojet disk, the probe comprising:
   a stem fastened to a support at a first end of the stem;
   a first multi-element sensor that performs an inspection, constrained to move with the stem and configured to be inserted into the circumferential slot; and
   a second multi-element sensor,
   wherein the first and second multi-element sensors are disposed back to back at a second end of the stem, and the stem is pivotable about an axis thereof such that in a first position of the probe, the first and second multi-element sensors are aligned with and insertable into the circumferential slot, and in a second position of the probe which is 90° about the axis of the stem from the first position, the first and second multi-element sensors abut corresponding side faces of the circumferential slot.

2. A probe according to claim 1, wherein the first and second multi-element sensors are urged resiliently in opposite directions, to provide contact between the multi-element sensors and the opposite surfaces for inspection.

3. A probe according to claim 2, wherein at least one spring is interposed between the first and second multi-element sensors.

4. A probe according to claim 1, wherein each multi-element sensor is of a shape that corresponds to a profile of the side face of the slot for inspection.

5. A probe according to claim 1, wherein the first and second multi-element sensors are held back to back and are connected to the stem by a sliding arrangement.

6. A method for eddy current inspection of a surface of a circumferential slot formed in a turbojet disk by a probe including a stem fastened to a support, the stem being pivotable about an axis thereof; and first and second multi-element sensors constrained to move with the stem and disposed back to back, and the stem is mounted to pivot about its own axis, the method comprising:
   a) positioning the first and second multi-element sensors in register with an opening of the slot so that a common axis of the sensors extends perpendicularly to an axis of the disk;
   b) moving the probe in a radial direction of the disk towards an inside of the slot so as to insert the first and second multi-element sensors in the slot;
   c) causing the stem to pivot through an angle of 90° so that the first and second multi-element sensors come into contact with side faces of the slot for inspection; and
   d) scanning an entire surface of the circumferential slot.

7. A method according to claim 6, wherein during the d) scanning, the probe remains stationary and the disk is turned through an angle of 360°.

8. A probe according to claim 1, wherein the first and second multi-element sensors are disposed along a common axis perpendicular to the axis of the stem.

9. A probe according to claim 8, wherein the common axis of the sensors is perpendicular to an axis of the disk in the first position of the probe, and the common axis of the sensors is parallel to the axis of the disk in the second position of the probe.

\* \* \* \* \*